United States Patent [19]

Kamijo et al.

[11] Patent Number: 5,023,261
[45] Date of Patent: Jun. 11, 1991

[54] ACYLATED BENZOFURO[3,2-C]QUINOLINE COMPOUNDS WITH UTILITY AS TREATMENTS FOR OSTEOPOROSIS

[75] Inventors: Tetsuhide Kamijo; Arao Ujiie; Hiromu Harada; Naoyuki Tsutsumi; Atsushi Tsubaki; Toshiaki Yamaguchi; Hideo Nagata, all of Nagano, Japan

[73] Assignee: Kissei Pharmaceutical Co., Ltd., Nagano, Japan

[21] Appl. No.: 321,248

[22] Filed: Mar. 9, 1989

[30] Foreign Application Priority Data

Aug. 30, 1988 [JP] Japan .................. 63-215755

[51] Int. Cl.$^5$ .................. C07D 471/00; A61K 31/44
[52] U.S. Cl. ...................... 514/285; 546/62
[58] Field of Search .................. 546/62; 514/285

[56] References Cited

FOREIGN PATENT DOCUMENTS

| 13391 | 8/1979 | Japan | 549/287 |
| 48924 | 8/1985 | Japan | 549/287 |
| 54379 | 8/1985 | Japan | 549/287 |
| 132917 | 12/1985 | Japan | 549/287 |
| 132976 | 12/1985 | Japan | 549/287 |

OTHER PUBLICATIONS

Yamaguchi et al., "Synth–Benzofuroquinolines", Het. Chem., vol. 21, pp. 737–739 (1984).
El-Mariah, "Potent. Non–Şteroidal Estrogens", Croatica Chem. Acta, vol. 59, No. 1, pp. 1781–176 (1986).
Bull. Chem. Soc. Jpn., vol. 53, pp. 1057–1060 (1980).

Primary Examiner—Nicholas S. Rizzo
Assistant Examiner—E. C. Ward
Attorney, Agent, or Firm—Sughrue, Mion, Zinn Macpeak & Seas

[57] ABSTRACT

Benzofuro[3,2-c]quinoline compounds of the general formula:

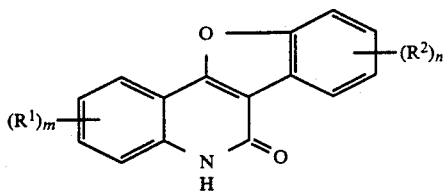

wherein
(1) each of $R^1$ and $R^2$ is the same, and represent a group of the formula of $-OR^3$ in which $R^3$ represents a carbamoyl group, an N-mono-alkylcarbamoyl group, an N,N-dialkylcarbamoyl group, an alkylsulfonyl group, a formyl group or an aliphatic acyl group which may have an alkoxycarbonyl group as a substituent; m represents zero, 1 or 2; n represents zero or 1; with the proviso that n is not zero when m is zero,
(2) each of $R^1$ and $R^2$ is different, and represent a hydroxy group or an N,N-di-alkylcarbamoyloxy group; m represents 1 or 2; n represents 1, possess a strong inhibitory action on bone resorption and a stimulatory effect on ossification. Some benzofuro[3,2-c]quinoline compounds of the above general formula also possess a stimulatory effect on longitudinal bone growth, and thus are useful for the prevention or treatment of osteoporosis.

10 Claims, No Drawings

ACYLATED BENZOFURO[3,2-C]QUINOLINE COMPOUNDS WITH UTILITY AS TREATMENTS FOR OSTEOPOROSIS

FIELD OF THE INVENTION

The present invention relates to benzofuro[3,2-c]quinoline compounds which are useful as a therapeutic agent. More particularly, the present invention relates to novel benzofuro[3,2-c]quinoline compounds represented by the general formula:

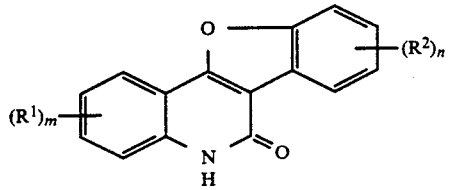

wherein
(1) each of $R^1$ and $R^2$ is the same, and represent a group of the formula of $-OR^3$ in which $R^3$ represents a carbamoyl group, an N-mono-alkylcarbamoyl group, an N,N-dialkylcarbamoyl group, an alkylsulfonyl group, a formyl group or an aliphatic acyl group which may have an alkoxycarbonyl group as a substituent; m represents zero, 1 or 2; n represents zero or 1; with the proviso that n is not zero when m is zero,
(2) each of $R^1$ and $R^2$ is different, and represent a hydroxy group or an N,N-dialkylcarbamoyloxy group; m represents 1 or 2; n represents 1, which are useful for the prevention or treatment of osteoporosis.

BACKGROUND OF THE INVENTION

Osteoporosis is a diseased condition or illness wherein the quantitative loss of bones has progressed beyond a certain limit with no substantial change in the chemical composition of the bones. A decrease in the amount of protein, calcium and phosphorus in bones is its physiological feature. Osteoporosis is increased with aging, and is observed most commonly in the elderly. The disease usually invades the vertebrae, and induces dorsal lumbago and shortening of a height. Especially, in the advanced case, the disease invades the long bones. Therefore, fracture often occurs in patients suffering from osteoporosis. It is thought that femur fractures observed in old women and men is almost always caused by osteoporosis. Pathogenic factors in the disease are varied, including endocrine disorder and nutritional disorder. Therapeutic agents such as vitamin $D_3$, calcium preparations, calcitonin, and phosphorus preparations are employed in the prevention or treatment of osteoporosis, but these are limited in effect to a given subject and can hardly be expected to show a definite effect. Therefore, it has long been desired to develop a pharmaceutical agent having a significant effect.

Recently, it has been reported that a certain compound of 3-phenyl-4H-1-benzopyran-4-ones which is different from the above agents is useful as a therapeutic agent for the prevention or treatment of osteoporosis in Japanese Patent Publication No. 13391/79 and Japanese Patent Application (OPI) Nos. 48924/85, 54379/85, 132917/85, 132976/85. (The term "OPI" as used herein refers to an unexamined Japanese patent application).

Up to now, with regard to benzofuro[3,2-c]quinoline compounds related to those of the present invention, the compounds represented by the following formulae (A) and (B) have been disclosed in Bulletin of the Chemical Society of Japan, Vol. 53, pages 1057–1060 (1980), Journal of Heterocyclic Chemistry, Vol. 21, pages 737–739 (1984).

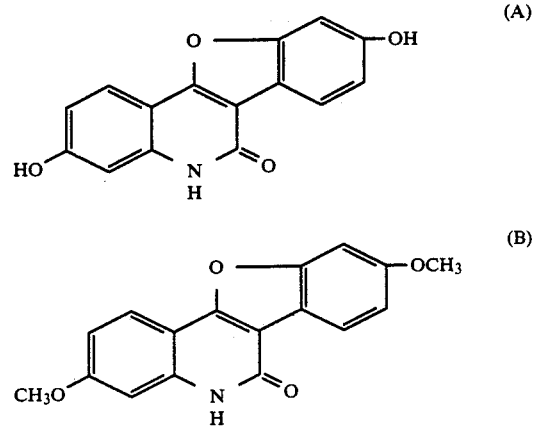

These compounds were prepared in order to investigate their chemical reactivities and to test their activities as mutagens, carcinogens, and anti-tumor substances, but there is no specific disclosure as to their pharmacological activities in these references. Furthermore, it has not been reported in any literature references that any benzofuro[3,2-c]quinoline compounds are useful for the prevention or treatment of osteoporosis.

The present inventors have investigated to find effective drugs for the prevention or treatment of osteoporosis. As a result, the inventors have found that certain benzofuro[3,2-c]quinoline compounds exhibit a strong inhibitory action on bone resorption and a stimulatory effect on ossification, and thus that they are useful as therapeutic agents for the prevention and treatment of osteoporosis.

Furthermore, the inventors have found that some compounds of the present invention also exhibit a strong stimulatory effect on longitudinal bone growth. Therefore, they are more useful as the therapeutic agent stated above.

CROSS REFERENCE

Some inventors of the present invention also have filed U.S. patent application Ser. No. 198,270 regarding to benzofuro[3,2-c]quinoline compounds related to those of the present invention.

SUMMARY OF THE INVENTION

An object of the present invention is to provide novel benzofuro[3,2-c]quinoline compounds which exhibit a strong inhibitory action on bone resorption and stimulatory effects on ossification and longitudinal bone growth.

Another object of the present invention is to provide pharmaceutical compositions comprising a benzofuro[3,2-c]quinoline compound.

Other objects, features and advantages of the present invention will be apparent from the following description of the invention.

DETAILED DESCRIPTION OF THE INVENTION

The present invention provides benzofuro[3,2-c]quinoline compounds which exhibit an inhibitory action on bone resorption and a stimulatory effect on ossification. Some benzofuro[3,2-c]quinoline compounds of the present invention also exhibit a stimulatory effect on longitudinal bone growth.

Thus, the benzofuro[3,2-c]quinoline compounds of the present invention are useful as therapeutic agents for the prevention or treatment of osteoporosis.

The term "alkyl" as used herein means a straight- or branched-chain alkyl group having 1 to 6 carbon atoms.

The term "aliphatic acyl" as used herein means a straight- or branched-chain aliphatic acyl group having 2 to 7 carbon atoms.

The term "alkoxycarbonyl" as used herein means a straight- or branched chain alkoxycarbonyl group having 2 to 7 carbon atoms.

The benzofuro[3,2-c]quinoline compounds of the present invention are characterized by the presence of one to three substituents on the ring, which are selected from a carbamoyloxy group, an N-mono-alkyl carbamoyloxy group, an N,N-dialkylcarbamoyloxy group, an alkysulfonzloxy group, a formyloxy group, an aliphatic acyloxy group which may have an alkoxycarbonyl group as a substituent or a hydroxy group.

Of the substituents on the ring, an N,N-dialkyl carbamoyloxy group and an aliphatic acyloxy group are preferable, especially, an N,N-dimethylcarbamoyl oxy group and an acetoxy group are preferable.

That is, an N,N-dialkylcarbamoyl oxy group tends to show a stronger stimulatory effect on longitudinal bone growth. An acetoxy group tends to show a stronger inhibitory effect on bone resorption and a stronger stimulatory effect on bone on ossification.

The substituents on the ring may be in any positions, but compounds having substituents at the 3 and 9 positions are preferable.

Of the benzofuro[3,2-c]quinoline compounds of the present invention, 3,9-bis(N,N-dimethylcarbamoyloxy)5H-benzofuro[3,2-c]quinolin-6-one, and 3,9-bis-(acetoxy)5H-benzofuro[3,2-c]quinolin-6-one one are the most preferable.

The benzofuro[3,2-c]quinoline compounds of the present invention can be prepared according to methods known per se. That is, the benzofuro[3,2-c]quinoline compounds of the present invention represented by the formula (I):

(I)

wherein
(1) each of $R^1$ and $R^2$ is the same, and represent a group of the formula —$OR^3$ in which $R^3$ represents a carbamoyl group, an N-mono-alkylcarbamoyl group, an N,N-dialkylcarbamoyl group, an alkylsulfonyl group, a formyl group or an aliphatic acyl group which may an alkoxycarbonyl group as a substituent; m represents zero, 1 or 2; n represents zero or 1; with the proviso that n is not zero when m is zero, (2) each of $R^1$ and $R^2$ is different, and represent a hydroxy group or an N,N-dialkylcarbamoyloxy group; m represents 1 or 2; n represents 1, can be prepared from the compounds represented by the formula (II):

(II)

wherein $R^4$ represents a hydroxy group; m represents zero, 1 or 2; n represents zero or 1; with the proviso that n is not zero when m is zero.

That is, of the compounds represented by the formula (I) of the present invention, the compounds having one to three formyloxy or aliphatic acyloxy groups on the ring as substituents can be prepared by treating a carboxylic acid compound represented by the formula (III):

$R^5$—COOH       (III)

wherein $R^5$ represents a hydrogen atom or an alkyl group, with 1,1'-carbonyldiimidazole and methyl iodide in chloroform, and then adding a solution of the compound represented by the formula (II) in N,N-dimethylformamide or dimethylsulfoxide.

Of the compounds represented by the general formula (I) of the present invention, the compounds having one to three aliphatic acyloxy groups which may have an alkoxycarbonyl group as a substituent, alkylsulfonyloxy or N,N-dialkylcarbamoyloxy groups can be prepared by treating the compound represented by the formula (II) with a compound represented by the formula (IV):

$R^6$—X       (IV)

wherein $R^6$ represents an aliphatic acyl group which may have an alkoxycarbonyl group as a substituent, an alkylsulfonyl group or an N,N-dialkylcarbamoyl group; X represents a halogen atom, using 4-dimethylaminopyridine as a catalyst in the presence of a basic substance in N,N-dimethylformamide.

Of the compounds represented by the formula (I) of the present invention, the compounds having one to three carbamoyloxy or N-mono-alkylcarbamoyloxy groups can be prepared by reacting the compound represented by the formula (II) with an isocyanate compound represented by the formula (V):

$R^7$—N=C=O       (V)

wherein $R^7$ represents an alkyl group or a chlorosulfonyl group, in the presence of a basic substance in N,N-dimethylformamide, and then, if desired, treating the resulting compounds with water.

The compounds represented by the formula (II) used as starting materials in the present invention can be easily prepared by the method disclosed in the literature, for example, Bulletin of the Chemical Society of Japan, Vol. 53, pages 1057–1060, 1980; Journal of Heterocyclic Chemistry, Vol. 16, pages 487–491, 1979; ibidem, Vol. 21, pages 737–739, 1984 or an analogous method thereto.

The desired product can be isolated and purified in a conventional manner such as washing, recrystallization and silica gel column chromatography.

The benzofuro[3,2-c]quinoline compounds represented by the formula (I) of the present invention possess a strong inhibitory action on bone resorption and a stimulatory effect on ossification, for example, the benzofuro[3,2-c]quinoline compounds produce a significant effect at a $10^{-5}$ molar concentration when determined by an in vitro experiment using the femur of a chick embryo. Furthermore, some benzofuro[3,2-c]quinoline compounds represented by the formula (I) of the present invention also possess a stimulatory effect on longitudinal bone growth.

The benzofuro[3,2-c]quinoline compounds of the formula (I) of the present invention can be administered in various dosage forms depending upon the intended therapy. Typical dosage forms which can be used are tablets, pills, powders, suspensions, emulsions, granules, capsules, suppositories, and injectable preparations.

In molding the pharmaceutical compositions into a tablet form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, and ethanol, and disintegrators such as laminaria and agar. The tablets, if desired, can be coated into sugar-coated tablets, gelatin-coated tablets, film-coated tablets, or tablets coated with two or more layers.

When the pharmaceutical composition is formulated into an injectable preparation, the resulting solution and suspension are preferably sterilized, and are isotonic with respect to blood. In making the pharmaceutical composition into a solution or suspension, all diluents customarily used in the art can be employed. Examples of suitable diluents are water, ethyl alcohol, propylene glycol, ethoxylated isostearyl alcohol, polyoxyethylene sorbitol, and sorbitan esters. Sodium chloride, glucose or glycerol can be incorporated into a therapeutic agent in an amount sufficient to prepare an isotonic solution. The therapeutic agent may further contain ordinary dissolving aids, buffers, pain-alleviating agents, and optionally, coloring agents, fragrances, flavors, sweeteners, and other pharmacologically active agents which are known in the art.

The dosage of the benzofuro[3,2-c]quinoline compounds of the present invention can be in the range from about 10 mg to 1,000 mg per adult human by oral administration per day, or from about 1 mg to 100 mg per adult human by parenteral administration per day in multiple doses depending upon the type of disease, the severity of the condition to be treated, and the like.

The present invention is further illustrated in more detail by way of the following Reference Examples and Examples. The melting points of the products obtained were uncorrected.

REFERENCE EXAMPLE 1

3-Hydroxy-5H-benzofuro[3,2-c]quinolin-6-one

A mixture of 2.7 g of m-anisidine and 5.32 g of diethyl 2-methoxyphenylmalonate in 20 ml of diphenyl ether was placed in a flask equipped with an air condenser, and heated at 270–290° C. for 2.5 hours. After cooling, to the reaction mixture there was added 80 ml of diethyl ether. The precipitates were collected by filtration, and washed with diethyl ether to obtain 5.39 g of 4-hydroxy-7-methoxy-3-(2-methoxyphenyl)-2-quinolone (yield: 90.7%).

melting point: >300° C.
IR (KBr): $\nu$co 1620 cm$^{-1}$
NMR (d$_6$-DMSO)
δ: 3.81(s, 3H), 3.92(s, 3H), 6.85–6.93(m, 2H), 7.00–7.25(m, 3H), 7.44(t, 1H), 7.90(d, 1H), 9.70(br-s, 1H), 11.31(s, 1H)

| | elemental analysis as C$_{17}$H$_{15}$NO$_4$ | | |
|---|---|---|---|
| | C% | H% | N% |
| Calcd. | 68.68 | 5.09 | 4.71 |
| Found | 68.79 | 5.08 | 4.72 |

In 640 ml of 47% hydrobromic acid was suspended 8.0 g of 4-hydroxy-7-methoxy-3-(2-methoxyphenyl)-2quinolone, and the suspension was heated under reflux for 3-4 days. After cooling, the precipitates were collected by filtration, washed with water, and dried to obtain 5.6 g of 3-hydroxy-5H-benzofuro[3,2-c]quinolin-6-one.

melting point: >300° C.
IR (KBr): $\nu$co 1640 cm$^{-1}$
NMR (d$_6$-DMSO)
δ: 6.92–7.04(m, 2H), 7.52–7.60(m, 2H), 7.89–8.17(m, 3H), 10.49(s, 1H), 11.88(s, 1H)

| | elemental analysis as C$_{15}$H$_9$NO$_3$ | | |
|---|---|---|---|
| | C% | H% | N% |
| Calcd. | 71.71 | 3.61 | 5.58 |
| Found | 71.37 | 3.61 | 5.44 |

REFERENCE EXAMPLE 2

The following compounds were prepared in a similar manner to that described in Reference Example 1 except that diethyl 2,4-dimethoxyphenylmalonate or diethyl 2,3-dimethoxyphenylmalonate was used in place of the diethyl 2-methoxyphenylmalonate.

3,9-Dihydroxy-5H-benzofuro[3,2-c]quinolin-6-one melting point: >300° C.
IR (KBr): $\nu$co 1640 cm$^{-1}$
NMR (d$_6$-DMSO)
δ: 6.90(dd, 1H), 6.95–7.05(m, 2H), 7.23(d, 1H), 7.91(d, 1H), 7.93(d, 1H), 10.00(s, 1H), 10.40(s, 1H), 11.80(s, 1H)

| | elemental analysis as C$_{15}$H$_9$NO$_4$ | | |
|---|---|---|---|
| | C% | H% | N% |
| Calcd. | 67.42 | 3.39 | 5.24 |
| Found | 67.24 | 3.41 | 5.35 |

3,10-Dihydroxy-5H-benzofuro[3,2-c]quinolin-6-one melting point: >300° C.
IR (KBr): $\nu$co 1640 cm$^{-1}$
NMR (d$_6$-DMSO)
δ: 6.85–7.15(m, 3H), 7.31(t, 1H), 7.99(d, 1H), 10.45(s, 2H), 11.83(s, 1H)

| elemental analysis as $C_{15}H_9NO_4$ | | | |
|---|---|---|---|
| | C% | H% | N% |
| Calcd. | 67.42 | 3.39 | 5.24 |
| Found | 67.25 | 3.26 | 5.13 |

REFERENCE EXAMPLE 3

The following compounds were prepared in a similar manner to that described in Reference Example 1 except that diethyl 2,4-dimethoxyphenylmalonate was used in place of diethyl 2-methoxyphenylmalonate and that aniline, o-anisidine, p-anisidine or 3,4-dimethoxyaniline were used in place of m-anisidine.

9-Hydroxy-5H-benzofuro[3,2-c]quinolin-6-one melting point: >300° C.
IR (KBr): $\nu$co 1650 cm$^{-1}$
NMR (d$_6$-DMSO)
δ: 7.00–7.35(m, 2H), 7.40–7.75(m, 3H), 7.99(d, 1H), 8.13(d, 1H), 10.11(s, 1H), 12.05(s, 1H)

| elemental analysis as $C_{15}H_9NO_3$ | | | |
|---|---|---|---|
| | C% | H% | N% |
| Calcd. | 71.71 | 3.61 | 5.58 |
| Found | 71.62 | 3.49 | 5.42 |

4,9-Dihydroxy-5H-benzofuro[3,2-c]quinolin-6-one melting point: >300° C.
IR (KBr): $\nu$co 1650 cm$^{-1}$
NMR (d$_6$-DMSO)
δ: 7.00–7.20(m, 2H), 7.25–7.35(m, 2H), 7.58(d, 1H), 7.99(d, 1H), 10.11(s, 1H), 10.63(s, 1H), 10.71(s, 1H)

| elemental analysis as $C_{15}H_9NO_4$ | | | |
|---|---|---|---|
| | C% | H% | N% |
| Calcd. | 67.42 | 3.39 | 5.24 |
| Found | 67.53 | 3.27 | 5.35 |

2,9-Dihydroxy-5H-benzofuro[3,2-c]quinolin-6-one melting point: >300° C.
IR (KBr): $\nu$co 1660 cm$^{-1}$
NMR (d$_6$-DMSO)
δ: 7.00–7.10(m, 1H), 7.15–7.55(m, 4H), 7.97(d, 1H), 9.81(s, 1H), 10.09(s, 1H), 11.83(s, 1H)

| elemental analysis as $C_{15}H_9NO_4$ | | | |
|---|---|---|---|
| | C% | H% | N% |
| Calcd. | 67.42 | 3.39 | 5.24 |
| Found | 67.47 | 3.35 | 5.29 |

2,3,9-Trihydroxy-5H-benzofuro[3,2-c]quinolin-6-one melting point: >300° C.
IR (KBr): $\nu$co 1650 cm$^{-1}$
NMR (d$_6$-DMSO)
δ: 6.95–7.10(m, 2H), 7.24(br-s, 1H), 7.36(s, 1H), 7.89(d, 1H), 9.20–10.50(br, 3H), 11.63(s, 1H)

| elemental analysis as $C_{15}H_9NO_5$ | | | |
|---|---|---|---|
| | C% | H% | N% |
| Calcd. | 63.61 | 3.20 | 4.95 |
| Found | 63.69 | 3.18 | 4.92 |

EXAMPLE 1

3,9-Bis(acetoxy)-5H-benzofuro[3,2-c]quinolin-6-one (Compound 1)

In 10 ml of dry N,N-dimethylformamide was dissolved mg of 3,9-dihydroxy-5H-benzofuro[3,2-c]quinolin-6-one, and 1.3 ml of triethylamine was added to the solution. Then, to the mixture were added 0.67 ml of acetyl chloride and a catalytic amount of 4-dimethylaminopyridine, and the mixture was stirred overnight at room temperature. The reaction mixture was poured into 180 ml of water, and the precipitates were collected by filtration, washed with diethyl ether, and dried under reduced pressure to obtain 630 mg of 3,9-bis(acetoxy)-5H-benzofuro[3,2-c]quinolin-6-one as a pale yellow powder.

melting point: 270° C. (decomposition)
IR (KBr): $\nu$co 1760, 1670 cm$^{-1}$
NMR (d$_6$-DMSO)
δ: 2.45(s,6H), 7.25–7.50(m, 3H), 7.87(br-s, 1H), 8.15–8.30(m, 2H), 12.25(br-s, 1H)

EXAMPLE 2

The following compounds were prepared in a similar manner to that described in Example 1.

3,9-Bis(propionyloxy)-5H-benzofuro[3,2-c]quinolin-6-one (Compound 2)

melting point: 252°–267° C.
IR (KBr): $\nu$co 1750, 1660 cm$^{-1}$
NMR (d$_6$-DMSO)
δ: 1.20–1.40(m, 6H), 2.70–2.90(m, 4H), 7.25–7.50(m, 3H), 7.86(d, 1H), 8.15–8.30(m, 2H), 12.24(s, 1H)

3,9-Bis(ethoxycarbonylpropionyloxy)-5H-benzofuro[3,2-c]quinolin-6-one (Compound 3)

melting point: 192°–196° C.
IR (KBr): $\nu$co 1760, 1730, 1660 cm$^{-1}$
NMR (d$_6$-DMSO)
δ: 1.33(t, 6H) 2.75–3.10(m, 8H), 4.23(q, 4H), 7.20–7.45(m, 3H), 7.82(br-s, 1H), 8.20–8.30(m, 2H), 12.26(br-s, 1H)

EXAMPLE 3

3,9-Bis(formyloxy)-5H-benzofuro[3,2-c]quinolin-6-one (Compound 4)

To a solution of 0.35 ml of formic acid in 10 ml of dry chloroform were added 1.5 g of 1,1'-carbonyldiimidazole and 1.74 ml of methyl iodide, and the mixture was stirred at room temperature for 2.5 hours. To the reaction mixture was added a solution of 0.5 g of 3,9-dihydroxy-5H-benzofuro[3,2-c]quinolin-6-one in 10 ml of dry N,N-dimethylformamide, and the mixture was stirred overnight at room temperature. To the reaction mixture was added 30 ml of water, and the precipitates were collected by filtration, washed with ethyl acetate, and dried at 60° C under reduced pressure to obtain 0.54 g of 3,9-bis(formyloxy)-5H-benzofuro[3,2-c]quinolin-6-one.

IR (KBr): $\nu$co 1730, 1680, 1650 cm$^{-1}$

NMR (d₆-DMSO)
δ: 7.30–7.55(m, 3H), 7.99(s, 1H), 8.20–8.30(m, 2H), 8.70–8.80(m, 2H), 12.28(s, 1H)

EXAMPLE 4

3,9-Bis(methylsulfonyloxy)-5H-benzofuro[3,2-c]quinolin-6-one (Compound 5)

In dry N,N-dimethylformamide was dissolved 500 mg of 3,9-dihydroxy-5H-benzofuro[3,2-c]quinolin-6-one. To the solution were added successively 1.3 ml of triethylamine, 0.72 ml of methylsulfonyl chloride and 10 mg of -dimethylaminopyridine, and the mixture was stirred overnight at room temperature. The reaction mixture was diluted with water, and the precipitates were collected by filtration, washed with water and ether, and dried to obtain 725 mg of 3,9-bis(methylsulfonyloxy)-5H-benzofuro[3,2-c]quinolin-6-one.
melting point: >300° C.
IR (KBr): νco 1670 cm⁻¹
NMR (d₆-DMSO)
δ: 3.58(s, 3H), 3.62(s, 3H), 7.45–7.70(m, 3H) 8.00–8.15(m, 1H), 8.20–8.35(m, 2H), 12.31(s, 1H)

EXAMPLE 5

3,9-Bis(carbamoyloxy)-5H-benzofuro[3,2-c]quinolin-6-one (Compound 6)

In 10 ml of dry N,N-dimethylformamide was suspended 500 mg of 3,9-dihydroxy-5H-benzofuro[3,2-c]quinolin-6-one. To the suspension were added successively 1.3 ml of triethylamine and 0.81 ml of chlorosulfonyl isocyanate, and the mixture was stirred overnight at room temperature. Into the reaction mixture was poured 20 ml of water, and the mixture was stirred for another 3 hours. Into the reaction mixture was poured 80 ml of water. The precipitates were collected by filtration, washed with ether, and dried under reduced pressure to obtain 665 mg of 3,9-bis(carbamoyloxy)-5H-benzofuro[3,2-c]quinolin-6-one as a yellow brown powder.
melting point: 215°–220° C.
IR (KBr): νco 1780, 1710, 1660 cm⁻¹

EXAMPLE 6

3,9-Bis(N-methylcarbamoyloxy)-5H-benzofuro[3,2-c]quinolin-6-one (Compound 7)

In 15 ml of dry N,N-dimethylformamide was suspended 500 mg of 3,9-dihydroxy-5H-benzofuro[3,2-c]quinolin-6-one. To the suspension were added 0.55 ml of methyl isocyanate and 1.7 ml of triethylamine, and the mixture was stirred overnight at room temperature. To the reaction mixture were added 0.33 ml of methyl isocyanate and 0.78 ml of triethylamine, and the mixture was poured into 180 ml of water. The precipitates were collected by filtration, washed with ether, and dried under reduced pressure to obtain 593 mg of 3,9-bis(N-methylcarbamoyloxy)-5H-benzofuro[3,2-c]quinolin-6-one.
melting point: >300° C.
IR (KBr): νco 1720, 1670 cm⁻¹

EXAMPLE 7

3,9-Bis(N,N-dimethylcarbamoyloxy)-5H-benzofuro[3,2-c]quinolin-6-one (Compound 8)

In 450 ml of dry N,N-dimethylformamide was dissolved 21 g of 3,9-dihydroxy-5H-benzofuro[3,2-c]quinolin-6-one. To the solution were added successively 55 ml of triethylamine, 41 g of dimethylcarbamyl chloride and 500 mg of 4-dimethylaminopyridine, and the mixture was stirred overnight at room temperature. The reaction mixture was diluted with water. The precipitates were collected by filtration, washed with water and ether, and dried to obtain 30 g of 3,9-bis(N,N-dimethylcarbamoyloxy)-5H-benzofuro[3,2-c]quinolin-6-one as white crystals.
melting point: 255°–269° C.
IR (KBr): νco 1710, 1660 cm⁻¹
NMR (d₆-DMSO)
δ: 3.07(s, 6H), 3.15–3.25(m, 6H), 7.20–7.40(m, 3H), 7.83(br-s, 1H), 8.10–8.25(m, 2H), 12.19(br-s, 1H)

EXAMPLE 8

The following compounds were prepared in a similar manner to that described in Example 7 except that the corresponding hydroxy, dihydroxy or trihydroxy-5H-benzofuro[3,2-c]quinolin-6-one were used in place of 3,9-dihydroxy-5H-benzofuro[3,2-c]quinolin-6-one.

3-(N,N-Dimethylcarbamoyloxy)-5H-benzofuro[3,2-c]quinolin-6-one (Compound 9)

melting point: 282°–286° C.
IR (KBr): νco 1730, 1710, 1670 cm⁻¹
NMR (d₆-DMSO)
δ: 3.06(s, 3H), 3.20(s, 3H), 7.20–7.30(m, 1H), 7.38(d, 1H), 7.55–7.70(m, 2H), 7.97(d, 1H), 8.15–8.30(m, 2H), 12.17(s, 1H)

9-(N,N-Dimethylcarbamoyloxy)-5H-benzofuro[3,2-c]quinolin-6-one (Compound 10)

melting point: 275°–280° C. (decomposition)
IR (KBr): νco 1720, 1660 cm⁻¹
NMR (d₆-DMSO)
δ: 3.06(s, 3H), 3.21(s, 3H), 7.35–7.55(m, 2H), 7.60–7.90(m, 3H), 8.15–8.25(m, 2H), 12.15(s, 1H)

4,9-Bis(N,N-Dimethylcarbamoyloxy)-5H-benzofuro[3,2-c]quinolin-6-one (Compound 11)

melting point: 236°–240° C. (decomposition)
IR (KBr): νco 1720, 1660 cm⁻¹
NMR (d₆-DMSO)
δ: 3.00–3.30(m, 12H), 7.35–7.60(m, 3H), 7.86(s, 1H), 8.00–8.15(m, 1H), 8.20(d, 1H), 11.93(s, 1H)

2,9-Bis(N,N-dimethylcarbamoyloxy)-5H-benzofuro[3,2-c]quinolin-6-one (Compound 12)

melting point: >300° C.
IR (KBr): νco 1720, 1660 cm⁻¹
NMR (d₆-DMSO)
δ: 3.07(s, 6H), 3.22(s, 6H), 7.30–7.70(m, 3H), 7.80–8.00(m, 2H), 8.18(d, 1H), 12.21(s, 1H)

3,10-Bis(N,N-dimethylcarbamoyloxy)-5H-benzofuro[3,2-c]quinolin-6-one (Compound 13)

melting point: 231°–236° C. (decomposition)
IR (KBr): νco 1720, 1680 cm⁻¹
NMR (d₆-DMSO)
δ: 3.00–3.40(m, 12H), 7.20–7.70(m, 4H), 8.00–8.30(m, 2H), 12.23(s, 1H)

2,3,9-Tris(N,N-dimethylcarbamoyloxy)-5H-benzofuro[3,2-c]quinolin-6-one (Compound 14)

melting point: 284°–289° C. (decomposition)
IR (KBr): νco 1720, 1660 cm⁻¹
NMR (d₆-DMSO)

δ: 3.00–3.30(m, 18H), 7.35–7.45(m, 1H), 7.52(s, 1H), 7.80–7.90(m, 1H), 8.04(s, 1H), 8.17(d, 1H), 12.23(s, 1H)

EXAMPLE 9

3-(N,N-Dimethylcarbamoyloxy)-9-hydroxy-5H-benzofuro[3,2-c]quinolin-6-one (Compound 15)

9-(N,N-Dimethylcarbamoyloxy)-3-hydroxy-5H-benzofuro[3,2-c]quinolin-6-one (Compound 16)

In 1.0 ml of dry N,N-dimethylformamide was dissolved 100 mg of 3,9-dihydroxy-5H-benzofuro[3,2-c]quinolin-6-one. To the solution were added successively 7.8 μl of triethylamine, 40 mg of dimethylcarbamyl chloride and 3 mg of 4-dimethylaminopyridine, and the mixture was stirred for 15 hours at room temperature. The reaction mixture was evaporated under reduced pressure. The residue was purified by preparative silica gel thin layer chromatography (developing solvent: chloroform/methanol/ethyl ether=10/$\frac{1}{2}$ by volume) to obtain 40 mg of 3-(N,N-dimethylcarbamoyloxy)-9-hydroxy-5H-benzofuro[3,2-c]quinolin-6-one and 25 mg of 9-(N,N-dimethylcarbamoyl)-3-hydroxy-5H-benzofuro[3,2-c]quinolin-6-one.

3-(N,N-Dimethylcarbamoyloxy)-9-hydroxy-5H-benzofuro[3,2-c]quinolin-6-one (Compound 15)

melting point: >240° C. (decomposition)
IR (KBr): νco 1700, 1660, 1630 cm$^{-1}$
NMR (d$_6$-DMSO)
δ: 3.27(s, 3H), 3.40(s, 3H), 7.20–7.35(m, 1H), 7.40–7.60(m, 3H), 8.19(d, 1H), 8.33(d, 1H), 10.33(s, 1H), 12.30(s, 1H)

9-(N,N-Dimethylcarbamoyloxy)-3-hydroxy-5H-benzofuro[3,2-c]quinolin-6-one (Compound 16)

melting point: >300° C.
IR (KBr): νco 1700, 1650 cm$^{-1}$
NMR (d$_6$-DMSO)
δ: 3.06(s, 3H), 3.21(s, 3H), 6.90–7.10(m, 2H), 7.30–7.40(m, 1H), 7.76(d, 1H), 8.00(d, 1H), 8.10(d, 1H), 10.5(br, 1H), 11.92(s, 1H)

EXAMPLE 10

Inhibitory effect on bone resorption

The inhibitory effect of various compounds on bone resorption was tested according to the method described in "Advanced Tissue Cultures For In Vitro Assay And Production"(pages 111–114, edited by Isao Yamane & Hiroyoshi Endo, Published by SOFT SCIENCE, Inc. Tokyo).

Femur was isolated from 10- to 11-day chick embryos. After being cleaned from adherent soft tissues, the preparation was precultivated in 1 ml of BGJb-HW2 culture medium containing benzofuro[3,2-c]quinoline compounds of the present invention at 37° C. for 24 hours using the roller-tube method. Each tested compound was dissolved in dimethylsulfoxide at a concentration of 0.01 M and the solution was diluted with the culture medium to make a final concentration of $10^{-5}$ M of those compounds. In the case of a control group, the same volume of dimethylsulfoxide was added.

On the next day, the precultivated femur was further cultivated for 2 hours at 37° C. in 1 ml of fresh culture medium containing 1 μCi/ml of $^{45}$CaCl$_2$ to label the bone mineral with $^{45}$Ca. Then, the cultivated bone was rinsed with phosphate-buffered saline warmed at 37° C. to remove $^{45}$Ca adhered to the bone. $^{45}$Ca-labelled bone was again cultivated using the roller-tube method, and the radioactivity of $^{45}$Ca in an aliquot of the culture medium was determined by a liquid scintillation counter at a point of 2, 24, 48 and 72 hours, respectively. The culture medium was freshed at each determination of the radioactivity. After completion of the cultivation, the bone was immersed in 1 ml of 1N HCl for 24 hours to elute all calcium in the bone, and the remaining radioactivity in the bone was determined.

From the obtained data, the rate of remaining radioactivity in the bone to the initial radioactivity in the bone was measured at each observation. Then the eluting rate of bone mineral by osteoclasts was obtained by linear-regression of decay curve for the rate of remaining radioactivity in the bone after 24 to 72 hours of the cultivation, and turnover rate of calcium in the bone mineral accumulated in the cultivated bone was estimated as the biological half-life ($T_{\frac{1}{2}}$).

In the case that $T_{\frac{1}{2}}$ of the test compound group of the present invention preparations is larger than that of the control group, such shows that these compounds have an inhibitory effect on bone resorption. The potency of the inhibition of the present invention's compounds was calculated by the following equation using $T_{178}$.

Inhibitory potency on bone resoprtion =

$$\frac{T_{\frac{1}{2}} \text{ of the test compound group}}{T_{\frac{1}{2}} \text{ of the control group}}$$

The results are shown in the following table as the means value of 5 observations.

| [Compounds] | [Inhibitory potency on bone resorption] |
| --- | --- |
| 1 | 1.83 |
| 2 | 1.59 |
| 3 | 1.52 |
| 4 | 1.54 |
| 5 | 2.00 |
| 6 | 1.74 |
| 7 | 1.63 |
| 8 | 1.41 |

EXAMPLE 11

Stimulatory effect on ossification

The stimulatory effect of various compounds on ossification was tested according to the method described in "Advanced Tissue Cultures For In Vitro Assay And Production" (pages 103–111, edited by Isao Yamane & Hiroyoshi Endo, Published by SOFT SCIENCE, Inc. Tokyo).

Femur was isolated from 9-day chick embryo. After being cleaned from adherent soft tissues, one femur of a paired femora was used for a test of a compound of the present invention, and the other femur was used as a test of a control group. One preparation was placed directly on the inner surface of a glass roller-tube, and 2 ml of BGJb-HW2 culture medium was added to each tube. Each preparation was cultivated at 37° C. by the roller-tube method for 6 days. During the cultivation, femur length was measured, and the culture medium was freshened every other day. Each tested compound was dissolved in dimethylsulfoxide at a concentration of 0.01 M and the solution was diluted by the culture medium to make a final concentration of $10^{-5}$ M of those compounds. In the case of the control group, the same volume of dimethylsulfoxide was added.

After completion of the cultivation, the bone was immersed in 1N HCl for 24 hours to elute all calcium in the bone, and the eluted calcium was determined by a chelating method using orthocresolphthalein.

The potency of the stimulatory effect on ossification of the present invention's compounds was calculated by the following equation.

Stimulatory potency on ossification =

$$\frac{\text{Amount of calcium in the test compound group}}{\text{Amount of calcium in the control group}}$$

The results are shown in the following table as the mean value of 6 observations.

| [Compounds] | [Stimulatory potency on ossification] |
|---|---|
| 1 | 1.34 |
| 2 | 1.21 |
| 3 | 1.20 |
| 4 | 1.39 |
| 5 | 1.16 |
| 6 | 1.23 |
| 7 | 1.24 |
| 8 | 1.22 |
| 9 | 1.08 |
| 10 | 1.05 |
| 11 | 1.07 |
| 13 | 1.06 |

The potency of the effect on the growth of femoral length of the present invention's compounds was calculated by the following equation.

Potency of the effect on the growth of femoral length =

$$\frac{\text{femoral length in the test compound group}}{\text{femoral length in the control group}}$$

The results are shown in the following table as the mean value of 6 observations.

| [Compounds] | [Potency on growth of femoral length] |
|---|---|
| 8 | 1.10 |
| 9 | 1.09 |
| 11 | 1.05 |
| 15 | 1.05 |

EXAMPLE 12

Acute toxicity test 3,9-Bis(N,N-dimethylcarbamoyloxy)-5H-benzofuro[3,2-c]quinolin-6-one suspended in 1% hydroxypropyl cellulose solution was administered orally for 14 days at doses of 200, 600, and 2000 mg/kg/day to 20 male Sprague Dawley rats 5 weeks of age. No death of animals and no induction of toxic symptom were observed during 14 days after the administration.

EXAMPLE 13

Tablets

10 Grams of 3,9-bis(N,N-dimethylcarbamoyloxy)-5H-benzofuro[3,2-c]quinolin-6-one were admixed with 95 g of lactose and 40 g of Indian corn starch and with 700 ml of a 5% aqueous solution of hydroxypropyl cellulose, and then dried. The dried mixture was admixed with 8 g of calcium carboxymethyl cellulose and 7 g of calcium stearate and the mixture was shaped into 1000 tablets.

What is claimed is:

1. A compound represented by the formula:

[chemical structure with $(R^1)_m$ and $(R^2)_n$ substituents on benzofuroquinolinone core]

wherein
(1) each of $R^1$ and $R^2$ is the same, and represents a group of the formula of $-OR^3$ in which $R^3$ represents a carbamoyl group, an N-mono-alkylcarbamoyl group, an N,N-dialkylcarbamoyl group, m an alkylsulfonyl group, a formyl group or an aliphatic acyl group which may have an alkoxycarbonyl group as a substituent; m represents zero, 1 or 2; n represents zero or 1; with the proviso that n is not zero when m is zero,
(2) each of $R^1$ and $R^2$ is different, and represents a hydroxy group or an N,N-dialkylcarbamoyloxy group; m represents 1 or 2; n represents 1.

2. A compound, as claimed in claim 1, represented by the formula:

[chemical structure with $(CH_3)_2N-CO-$ groups, subscript q]

wherein q represents 1 or 2.

3. A compound, as claimed in claim 1, represented by the formula:

[chemical structure with $R^8-CO-$ and $-OC-R^8$ groups]

wherein $R^8$ represents an alkyl group.

4. The compound, as claimed in claim 2, represented by the formula:

[chemical structure with two N,N-dimethylcarbamoyloxy groups]

5. The compound, as claimed in claim 3, represented by the formula:

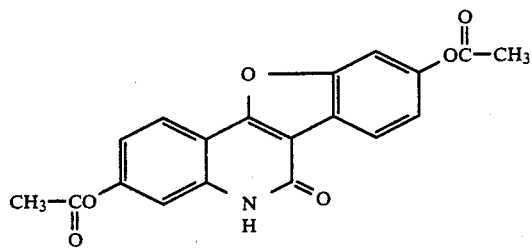

6. A pharmaceutical composition for the prevention or treatment of osteoporosis in bones comprising an inert pharmaceutical carrier and an effective amount of a compound represented by the formula:

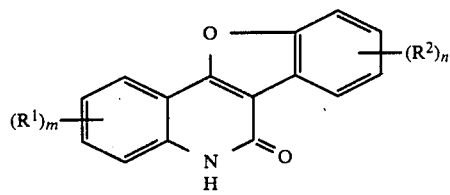

wherein
(1) each of $R^1$ and $R^2$ is the same, and represent a group of the formula of $-OR^3$ in which $R^3$ represents a carbamoyl group, an N-mono-alkylcarbamoyl group, an N,N-dialkylcarbamoyl group, an alkylsulfonyl group, a formyl group or an aliphatic acyl group which may have an alkoxycarbonyl group as a substituent; m represents zero, 1 or 2; n represents zero or 1; with the proviso that n is not zero when m is zero,
(2) each of $R^1$ and $R^2$ is different, and represent a hydroxy group or an N,N-dialkylcarbamoyloxy group; m represents 1 or 2; n represents 1.

7. A pharmaceutical composition, as claimed in claim 6, for the prevention or treatment of osteoporosis in bones comprising an inert pharmaceutical carrier and an effective amount of a compound represented by the formula:

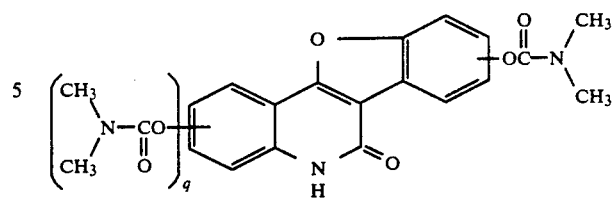

wherein q represents 1 or 2.

8. A pharmaceutical composition, as claimed in claim 6, for the prevention or treatment of osteoporosis in bones comprising an inert pharmaceutical carrier and an effective amount of a compound represented by the formula:

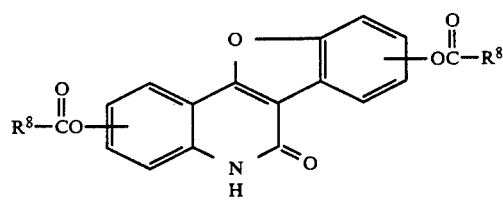

wherein $R^8$ represents an alkyl group.

9. A pharmaceutical composition, as claimed in claim 7, for the prevention or treatment of osteoporosis in bones comprising an inert pharmaceutical carrier and an effective amount of a compound represented by the formula:

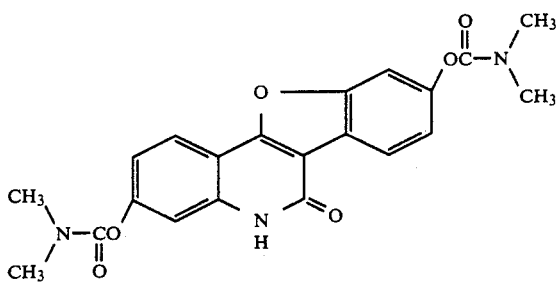

10. A pharmaceutical composition, as claimed in claim 8, for the prevention or treatment of osteoporosis in bones comprising an inert pharmaceutical carrier and an effective amount of a compound represented by the formula:

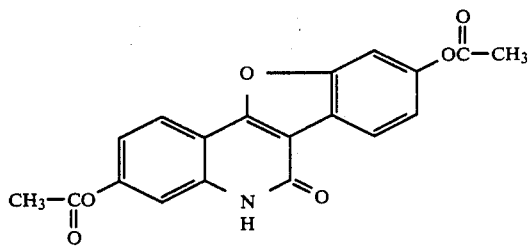

* * * * *